(12) United States Patent
Ueki et al.

(10) Patent No.: US 6,404,847 B1
(45) Date of Patent: Jun. 11, 2002

(54) CONTINUOUSLY SCANNING X-RAY ANALYZER HAVING IMPROVED READINESS AND ACCURACY

(75) Inventors: Bunjiro Ueki, Takatsuki; Toshiyuki Kato, Akishima; Hideaki Fujimoto, Takatsuki, all of (JP)

(73) Assignees: Rigaku Industrial Corporation, Osaka; Rigaku Corporation, Tokyo, both of (JP)

( * ) Notice: Subject to any disclaimer, the term of this patent is extended or adjusted under 35 U.S.C. 154(b) by 70 days.

(21) Appl. No.: 09/672,773

(22) Filed: Sep. 29, 2000

(30) Foreign Application Priority Data

Oct. 1, 1999 (JP) .......................................... 11-281418
Jul. 14, 2000 (JP) ...................................... 2000-214278

(51) Int. Cl.[7] .......................... G01N 23/223; G01T 1/36
(52) U.S. Cl. .............................. 378/45; 378/44; 378/45; 378/70; 378/71

(58) Field of Search .............................. 378/44, 45, 70, 378/71

(56) References Cited

U.S. PATENT DOCUMENTS 6,310,935 B1 * 10/2001 Kuwabara .................... 378/49

* cited by examiner

Primary Examiner—Robert H. Kim
Assistant Examiner—Courtney Thomas
(74) Attorney, Agent, or Firm—Sughrue Mion, PLLC

(57) ABSTRACT

An X-ray analyzing apparatus capable of accomplish a rapid and accurate analysis is provided in which a detector for X-rays is rotated or shuttled to perform a continuous scanning. Determining a counting time for each of fixed scanning intervals by means of a counting time counter 15 and a frequency divider 16, correction of a count for each scanning interval is made by a correction calculating means 11 on the basis of the corresponding counting time.

8 Claims, 8 Drawing Sheets

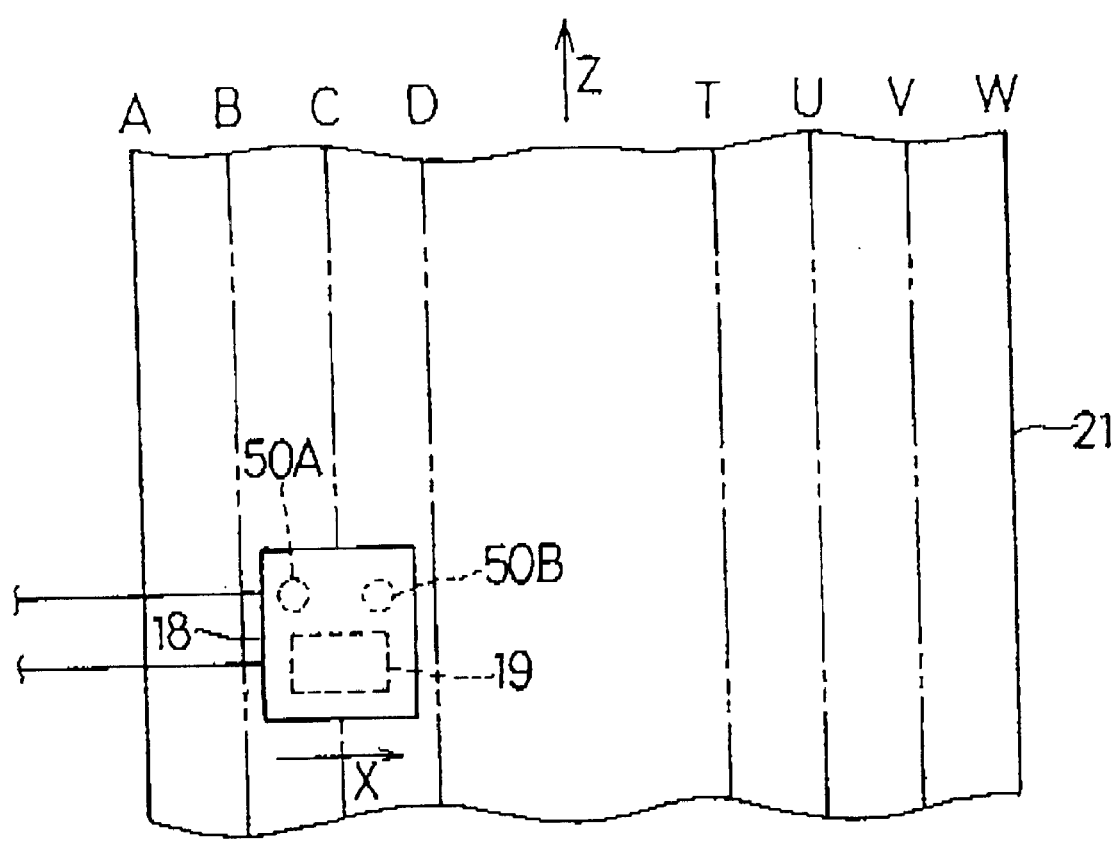

CONTINUOUSLY SCANNING X-RAY ANALYZER HAVING IMPROVED READINESS AND ACCURACY

BACKGROUND OF THE INVENTION 1. (Field of the Invention)

The present invention generally relates to an X-ray analysis apparatus whose detector part turns or shuttles to accomplish a continuous scanning.

2. (Description of the Prior Art)

In an X-ray fluorescence spectrometer of a wavelength dispersive type currently widely in use, a sample to be analyzed is irradiated by primary X-rays so that fluorescent X-rays are emitted from the sample. The fluorescent X-rays emitted from the sample are monochromated by a spectroscopic device such as an analyzing crystal, and the resultant, spectroscopically analyzed fluorescent X-rays are then detected by a detector which subsequently outputs pulses. Although the voltage of the pulses outputted from the detector, that is, the pulse height value is proportional to the fluorescent X-ray energy and the number of the output pulses per unitary time is proportional to the intensity of the fluorescent X-rays, of those output pulses the output pulses falling within a fixed range of pulse height values are selected by a pulse height analyzer and the number of those selected output pulses is counted by a scaler. In other words, the count of the selected output pulses is determined by a scaler.

In a scanning type of X-ray spectrometer, the spectroscopic device is scanned linked with the detector so that the wavelength of the monochromated X-rays change. One of the mechanism for the linkage is called as goniometer. Specifically where a qualitative analysis or a semi-quanfitative analysis is performed, the fist speed is required and, therefore, the spectroscopic device and the detector are continuously scanned. In other words, the scanning method is not step scan in which the goniometer is driven a predetermined angle and is then halted for a predetermined time during counting of the output pulses, but continuous scanning in which counting of the output pulses is carried out by continuously driving of the goniometer. At this time, for each fixed scanning interval, for example, ¹⁄₁₀₀ degree of the rotation angle of the detector (so-called 2θ) the scaler reads the count as an intensity for each scanning interval.

The relationship between the scanning range (2θ) of the goniometer and the scanning speed thereof is shown in FIG. 2. In order for the goniometer to be continuously driven at a desired high speed as shown by 'b' in FIG. 2, the goniometer has to be driven with accelerated speed as shown by 'a' in FIG. 2 before it is driven to the desired high speed. Also, to halt the goniometer being then driven at the high speed, the goniometer has to be driven with decelerated speed as shown by 'c' in FIG. 2. Accordingly, accurate intensity for each scanning interval can not be obtained in the ranges of accelerated and decelerated speed shown in 'a' and 'c', because the time required for each ¹⁄₁₀₀ degree varies.

On the other hand, if a method which counting is not performed in the ranges of the accelerated or decelerated speed shown by 'a' or 'c' is taken for accurate measurement, the analyses at each end can not be done. Also, if as shown by the chain double-dashed line counting is performed while the driving speed of the goniometer is lowered to such an extent that neither acceleration or deceleration is not required, an accurate analysis would be possible at both ends of the scanning range, but at the sacrifice of the speed.

Accordingly, rapid and accurate measurement of qualitative analysis or semi-quantitative analysis can not be done over a relatively wide range of wavelength.

In addition, in an X-ray diffractometer for analyzing the crystalline structure of sample, in which a sample support to place of the sample to be analyzed and a detector are linked by the goniometer so that the intensity of diffracted X-rays diffracted by the sample can be measured by varying the incident angle of X-rays irradiated upon the sample, a high precision measurement carried out by the step scan requires a relatively long time. On the other hand, the rapid measurement is possible by the continuous scan. However, accurate measurement is not possible because the counting time is not strictly constant for the fixed scanning interval.

While the foregoing description applies where the detector rotates on the spectroscopic device or the sample by the goniometer to accomplish the continuous scan, problems similar to those discussed above can be found even where a measurement unit including an X-ray source and a detector shuttles on a sample by the continuous scan. For example, in a production line in which while a strip of paper is transported in a direction lengthwise thereof a release agent such as silicone is coated on one surface of the strip of paper to form a strip of release coated paper which is subsequently cut longitudinally (in a direction conforming to the direction of transport) for each or sections divided equally in a widthwise direction thereof which is perpendicular to the longitudinal direction (or for each of continuous sections), to thereby provide a plurality of release coated papers, it is required for the purpose of a quality control of the products (i.e., release coated papers) that the amount of silicone coated is determined for each of the sections.

Accordingly, in the conventional X-ray fluorescence spectrometer designed to suit to the particular purpose discussed above, a measurement unit shuttles by a fixed speed on the sample, which is the strip of the release coated paper before being cut into the sections, in a direction widthwise of the strip of the release coated paper generates for unitary time a number of pulses proportional to the intensity of the fluorescent X-ray emitted from silicon as a result of the sample having been irradiated by a primary X-ray while being transported in the direction lengthwise thereof. Of the pulses generated from the measurement unit, the pulses falling within a predetermined pulse height range are selected by a pulse height analyzer and the number of the selected pulses is determined by a scaler. A calculating means for calculating the amount of silicone coated then determines the amount of silicone coated for each section, based on the measured intensity for each section which is obtained by dividing the number of the pulses generated by the measurement unit by the time required for the measurement unit to move a distance corresponding to one section at the fixed speed. It is here assumed that the moving speed of the measurement unit is constant and the time required for the measurement unit to move the distance corresponding to one section is also constant.

However, it has been found difficult to strictly maintain a constant value the speed at which the measurement unit is moved by the drive means, and the moving speed of the measurement unit varies to a certain extent. Consequently, association of the measured intensity with the particular section and, hence, association of the amount of silicon coated with the particular section tends to depart from each other and, therefore the amount of silicone coated cannot be accurately determined for each section.

SUMMARY OF THE INVENTION

Accordingly, the present invention is intended to provide an improved X-ray analyzing apparatus of a continuous scanning type in which a detector for detecting the intensity of X-rays is turned or shuttled, which apparatus is effective to achieve a rapid and accurate analysis.

To this end, the present invention provides an X-ray fluorescence spectrometer which includes a sample support of a sample to be analyzed; an X-ray source for irradiating the sample with a primary X-ray to excite the sample to emit a fluorescent X-ray therefrom; a spectroscopic device for monocromating the fluorescent X-ray emitted from the sample; a detector adapted to receive the fluorescent X-ray, which has been monochromated by the spectroscopic device, and to generate pulses of a voltage proportional to an energy of the fluorescent X-ray in a number proportional to an intensity of the fluorescent X-ray; and a linkage means for drivingly associating the spectroscopic device and the detector together to allow the sample to be continuously scanned, by causing the monochromated fluorescent X-rays to be incident upon the detector while a wavelength of the fluorescent X-ray monochromated by the spectroscopic device varies.

The X-ray fluorescence spectrometer referred to above also includes a pulse height analyzer for selecting the pulses which fall within a predetermined voltage range from the pulses generated by the detector, a scaler for the pulses selected by the pulse height analyzer; and a counting time counter for measuring the elapsed time in pulse counting by the scaler. The X-ray fluorescence spectrometer furthermore includes a frequency divider for generating a read-out signal for each of the predetermined scanning intervals in the linkage means. In response to the read-out signal from the frequency devider, the scaler reads the count and the counting time counter reads the counting time. The X-ray fluorescence spectrometer also includes a correction calculating means to correct the counts based on the counting time.

In the X-ray fluorescence spectrometer according to the present invention, since the counting time counter and the frequency divider are used to determine the counting time for each of the predetermined scanning intervals, and the count for each scanning interval is corrected by the correction calculating means on the basis of the corresponding counting time, an accurate intensity of the fluorescent X-ray for each scanning interval including the drive in the ranges of accelerated and decelerated speed can be obtained where the linkage means is driven at a high speed. Accordingly, in the fluorescent X-ray analysis, the qualitative analysis as well as the semi-quantitative analysis can be rapidly and accurately performed over a relatively wide range of wavelength. In other words, the rapid and accurate analysis is possible with the continuous scan.

In order to accomplish the foregoing object, the present invention also provides an X-ray diffractometer which includes a sample support to place a sample to be analyzed; an X-ray source for irradiating the sample with incident X-rays; a detector to generate pulses having the voltage proportional to the energy of the diffracted X-rays in a number proportional to the X-ray intensity; and a linkage means for linking the drive of the sample support with the detector to allow continuous scan so as that the diffracted X-rays irradiate the detector.

The X-ray difractometer referred to above also includes a pulse height analyzer for selecting the pulses which fall within a predetermined voltage range from the pulses generated by the detector, a scaler for counting the pulses selected by the pulse height analyzer; and a counting time counter for measuring the elapsed time in pulse counting by the scaler. The X-ray diffractometer futhermore includes a frequency divider for generating a read-out signal for each of the predetermined scanning intervals in the linkage means. In response to the read-out signal from the frequency devider, the scaler reads the count and the counting time counter reads the counting time. The X-ray diffractometer also includes a correction calculating means to correct the counts based on the counting time.

In the X-ray diffractometer according to the present invention, since the counting time counter and the frequency divider are used to determine the counting time for each of the predetermined scanning intervals, and the count for each scanning interval is corrected by the correction calculating means on the basis of the corresponding counting time, an accurate intensity of the diffracted X-ray for each scanning interval can be obtained and, accordingly, the rapid and accurate analysis is possible with the continuous scan in the X-ray diffraction analysis.

In order to accomplish the previously described object, the present invention furthermore provides an X-ray fluorescence spectrometer which includes a measuring unit for irradiating with primary X-rays a band-shaped sample made up with multi-layer film and being transported in a direction lengthwise thereof, to excite the sample to emit a fluorescent X-ray and for generating pulses in a number proportional to an intensity of the fluorescent X-ray emitted from the sample; a drive means for shuttling the measuring unit in a direction widthwise of the sample that is perpendicular to the lengthwise direction of the sample; and a sample edge detecting means mounted on the measuring unit for detecting each edge of the sample in the widthwise direction thereof.

The X-ray fluorescence spectrometer also includes a pulse height analyzer for selecting the pulses which fall within a predetermined voltage range from the measuring unit; a scaler for counting the pulses selected by the pulse height analyzer; a counting time counter for measuring the elapsed time in pulse counting by the scaler; a frequency divider for generating a read-out signal for each fixed moving range in the drive means, stating from a position where the sample edge detecting means detects one of the edges of the sample in the widthwise direction thereof. In response to the read-out signal from the frequency devider, the scaler reads the count and the counting time counter reads the counting time. The X-ray diffractometer also includes a correction calculating means to correct the counts based on the counting time; and a coating weight calculating means for determining a coating weight or thickness of at least one of the layers in the multi-layers, for each fixed moving range, based on the count corrected by the correction calculating means.

In the X-ray fluorescence spectrometer, since the correction calculating means corrects the count of the pulses generated by the measuring unit, based on the counting time which is the time required for the measuring unit to move, for each moving range on the sample in the widthwise direction thereon the coating weight or thickness can be rapidly and accurately determined for each section of the sample without the discrepancy in correspondence to each section in the sample even if the moving speed varies in high moving speed by setting the length of moving range in the widthwise direction. Thus, during the fluorescent X-ray analysis, the rapid and accurate analysis is possible with the continuous scanning.

The X-ray fluorescence spectrometer can be satisfactorily worked out where the sample is a release coated paper on which silicone is coated and the coating weight of thickness of silicone coated layer is analyzed. Or a magnetic tape which a magnetic material is coated and the coating weight or thickness of the magnetic material layer is analyzed.

Any one of the X-ray analyzing apparatuses described above according to the present invention, the like means or the moving means may have a rotary encoder so that the frequency divider can generate the read-out signal based on a signal fed from the rotary encoder.

BRIEF DESCRIPTION OF THE DRAWINGS

The present invention will become more clearly understood from the following description of preferred embodiments thereof, referring to the attached figures. However, the embodiments and the figures are given only for the purpose of illustration and explanation, and are not for limiting the scope of the present invention in any way whatsoever. The scope is to be determined by the appended claims. In the attached drawings, the same part number in more than one figure means same part, and:

FIG. 9 is a front view of the measurement unit employed in the X-ray fluorescence spectrometer of FIG. 5, which is located rightwards of a section B-C.

DETAILED DESCRIPTION OF THE EMBODIMENTS

Figure 1:
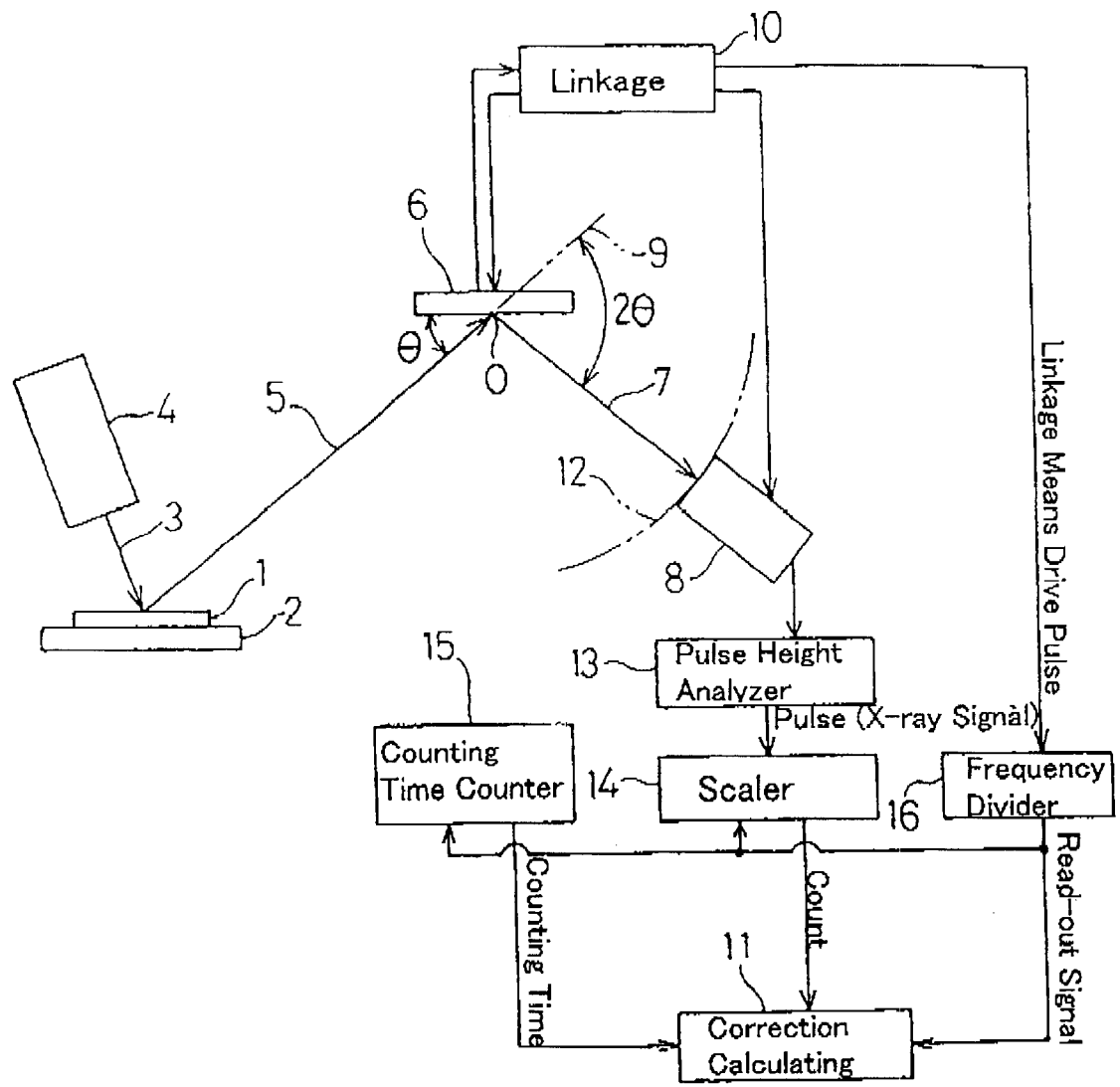
FIG. 1 is a schematic diagram showing an X-ray fluorescence spectrometer of the first preferred embodiment in the present invention.

Hereinafter, an apparatus according to the first preferred embodiment of the present invention will be described. In the first place, the structure of the apparatus will be described with reference to FIG. 1. The apparatus shown therein is an X-ray fluorescence spectrometer which includes a sample support 2 on which a sample 1 to be analyzed is placed; a X-ray source 4 such as an X-ray tube for irradiating the sample 1 with primary X-rays 3; a spectroscopic device 6 for monochromated fluorescent X-rays 5 emitted from the sample 1; a detector 8 such as SC or F-PC to detect the fluorescent X-rays 7 which has been monochromated by the spectroscopic device 6 and to generate pulses with voltage proportional to the energy of the fluorescent X-rays 7 in a number proportional to the intensity thereof; and a linkage means 10 such as a goniometer for linking the drive of the spectroscopic device 6 and the detector 8 to accomplish a continuous scan and change the wavelength of the fluorescent X-rays 7, monochromated by the spectroscopic device 6, so that the monochromized fluorescent X-rays 7 can irradiated on the detector 8.

In other words, when the fluorescent X-rays 5 irradiate upon the spectroscopic device 6 at a certain incident angle θ, an extension line 9 of the fluorescent X-rays 5 and the fluorescent X-rays 7 monochromated (diffracted) by the spectroscopic device 6 forms a diffracted angle 2θ which is twice the incident angle θ. However, the linkage means 10 rotates the spectroscopic device 6 about an axis O that passes the center of the surface of the spectroscopic device 6 and lies in the a direction perpendicular to the plane of a sheet of FIG. 1, and, also, rotates the detector 8 along the circular path 12 on the axis O by the angle that is twice the angle of rotation of the spectroscopic device, so that the monocromated fluorescent X-rays 7 can continue to irradiate on the detector 8 while the wavelength of the fluorescent X-rays 7 that are monochromized is varied by varying the diffracted angle 2θ. More specifically, each of the θ axis for rotating the spectroscopic device 6 and the 2θ axis for turning the detector 8 is provided with a pulse motor, a worm gear mounted on the drive shaft of the pulse motor and a worm wheel meshed with such worm gear and having the spectroscopic device 6 or the detector 8 fitted thereto, and the pulse motors for the θ axis and the 2θ axis, respectively, are electrically linked with each other in pulse start timing and pulse number control. The whole of these mechanisms is the linkage means 10.

Also, the apparatus includes a pulse height analyzer 13 for selecting the pulses generated by the detector 8 which fall within a fixed range of voltage (pulse height); a scaler 14 for counting the pulses selected by the pulse height analyzer 13; and a counting time counter 15 for measuring the counting time for the scaler 14 based on a reference pulse supplied from a quart oscillator or the like. In addition, this apparatus further more includes a frequency divider 16 for generating a readout signal for each of fixed scanning intervals for the linkage means 10, and a correction calculating means that corrects the count read-out by the scaler 14 based on the counting time measured by the counting time counter 15 in response to the read-out signal from the frequency driver 16.

More specifically, where, for example, one pulse supplied to the pulse motor that drives the linkage means 10 corresponds to $5/1,000$ degree in terms of 2θ, the frequency divider 16 in response to linkage means drive pulses supplies the read-out signal to the correction calculating means 11 every two pulses, that is $1/100$ degree in terms of 2θ for a fixed scanning interval in the linkage means 10, whereupon the correction calculating means 11 reads out the count given by the scaler 14 and the counting time measured by the counting time counter 15 every $1/100$ degree in terms of 2θ, so that the count can be corrected by dividing it by the counting time. The corrected count is the intensity of the fluorescent X-ray for that scanning interval. It is to be noted that the fixed Scanning interval can be preset within the range of for example, $1/100$ to $1/10$ degree.

Although in the illustrated embodiment the frequency divider 16 generates the read-out signal based on the linkage means drive pulse, the frequency driver 16 can generate the read-out signal in response to the signal from a rotary encoder equipped in the preciously described e axis or the 2θ axis of the linkage means 10.

The operation of the apparatus will now be described in the qualitative analysis. When the sample 1 has been placed on the sample support 2, the primary X-ray 3 is irradiated from the X-ray source 4, the fluorescent X-rays 5 generated from the sample 1 are monochromated by the spectroscope device 6 and the monochromated fluorescent X-rays 7 subsequently irradiate upon the detector 8 which in turn outputs pulses of voltage proportional to the energy of the incident fluorescent X-rays 7 in a number proportional to the intensity thereof. Of those pulses the pulses within a fixed voltage range are selected by the pulse height analyzer 13 and the count of the selected pulses is then determined by the scaler 14.

Figure 2:
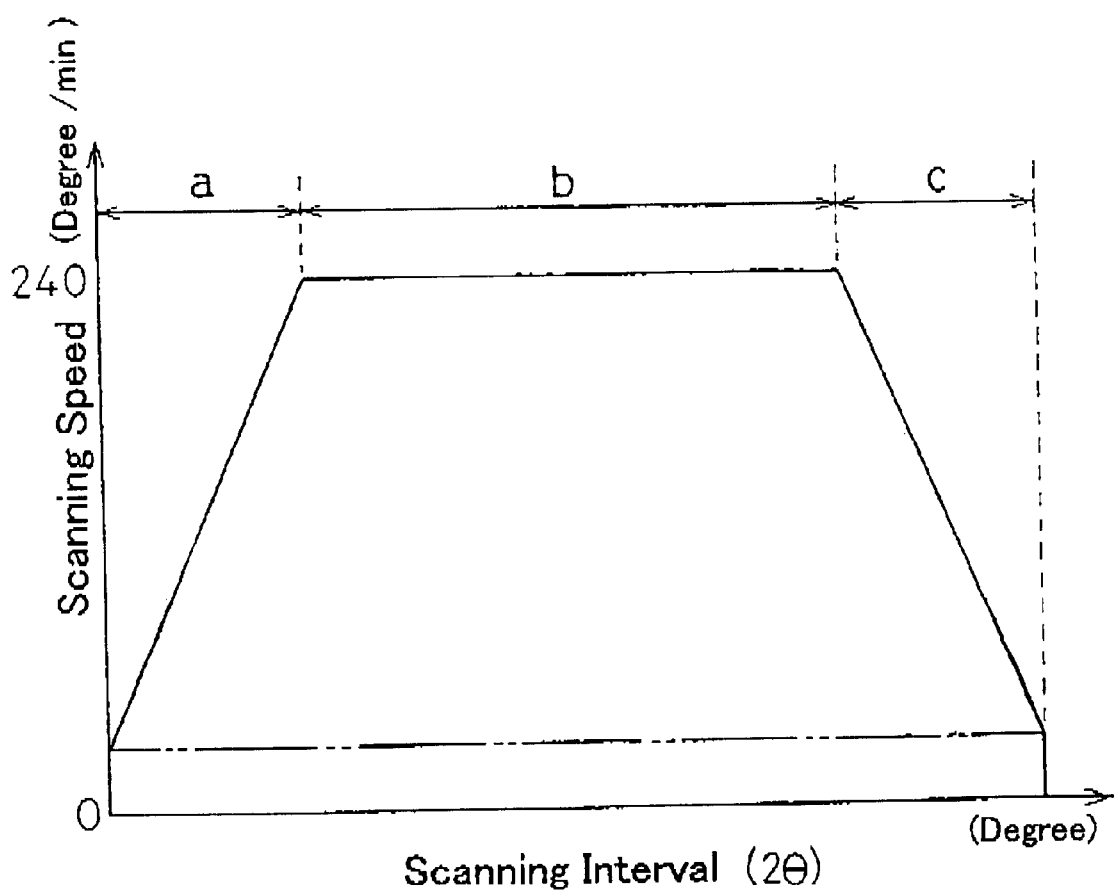
FIG. 2 is a chart showing the relationship between the scanning range (2θ) of a goniometer (a linkage means) and the scanning speed thereof.

While in this instance the drive the spectroscopic device 6 and the detector 8 is linked by the linkage means 10 to effect a continuous scan so that the fluorescent X-ray 5 generated from the sample 1 can be monochromated and the wavelength detected is scanned, the linkage means 10 is driven to attain a scanning speed of 240 degrees per minute in terms of 2θ as shown by 'b' in FIG. 2 for the purpose of speed. It is to be noted that numeric values to be assigned to the scanning range (2θ) for the axis of abscissas in the graph of FIG. 2 are not described since they vary depending on the particular type of the detector 8 and the spectroscopic device 6 (FIG. 1), the scanning range from the left end to the right end is about 100 degrees at maximum.

As described hereinbefore, in order to drive at such a high speed, drivings with accelerated speed and decelerated speed are required prior to and after the high speed drive, respectively, for example, over about 5 degrees (It is to be noted that FIG. 2 is shown exaggerated for better understanding) in terms of the scanning range (2θ). The counting time required for each scanning interval differs in the ranges of accelerated and decelerated speed even when the count is read-out from the scaler 14 for a fixed scanning interval of $1/100$ degree by using the frequency driver 16 shown in FIG. 1. On the other hand, the number per unitary time of the pulses entering the scaler 14 is proportional to the intensity of the fluorescent X-ray 7. Accordingly, the count for each fixed scanning interval read from the scaler does not represent an accurate intensity of the fluorescent X-rays in the ranges of the accelerated and decelerated speed.

In the apparatus, the counting time counter 15 measures the counting time required for the scaler 14 to count the number of the pulses, and the correction calculating means 11 reads out not only the count given by the scaler 14, but also the counting time measured by the counting time counter 15 in response to the read-out signal from the frequency divider 16 for a fixed scanning interval of $1/100$ degree. In this way, the counting time for each scanning interval of $1/100$ degree can be determined. On the other hand, the correction calculating means 11 corrects the count given by the scaler 14 by dividing it by the counting time measured by the counting time counter 15 for each scanning interval of $1/100$ degree. The corrected count consequently represents the intensity of the fluorescent X-ray for that scanning interval.

Thus, a spectrum representing the intensity of the fluorescent X-rays 7 at each diffracted angle 2θ can be obtained, and peak search and elemental identification are carried out, that is, the qualitative analysis is carried out. The result of the qualitative analysis is displayed by means of a display means such as a cathode ray tube (CRT) (not shown). Also, based on the result of the qualitative analysis, a so-called semi-quantitative analysis can be performed. Besides, the counting time correction is carried out in entire range without checking whether the scanning speed is constant or not. However, the correction may be carried out only in the driving ranges of accelerated and decelerated speed (shown by 'a' and 'c' in FIG. 2) assuming the scanning speed in the range of constant high speed (shown by 'b' in FIG. 2) as 1.

As described above, with the apparatus according to the first embodiment of the present invention, the counting time counter 15 and the frequency divider 16 are used to determine the counting time for a fixed scanning interval of, for example, $1/100$ degree, and the correction calculating means 11 is used to correct the count for each scanning interval based on the corresponding counting time. Accordingly, when the linkage means 10 is driven at a high speed, an accurate intensity of the fluorescent X-ray for each scanning interval including in the driving ranges of accelerated and decelerated speed (shown by 'a' and 'c' in FIG. 2) can be obtained. Accordingly, the qualitative analysis or the semi-quantitative analysis can be rapidly and accurately performed over the relatively wide range of wavelength in the fluorescent X-ray analysis. In other words, a rapid and accurate analysis is possible with the continuous scanning feature.

Besides, the linkage means 10 is driven by the pulse motor in the apparatus described as the foregoing first embodiment, a servo motor may be employed in place of the pulse motor. In this case, it is better to correct the entire scan range without checking whether the speed is constant or not for the correction since the speed may vary slightly even in constant high speed driving (shown by 'b' in FIG. 2).

The apparatus according to the second preferred embodiment of the present invention will now be described. This apparatus is an X-ray diffractometer which includes, as shown in FIG. 3, a sample support 2 on which a sample 1 to be analyzed is placed, an X-ray source 4 such as an X-ray tube for irradiating the sample 1 with incident X-rays (which is monochromated in most cases) 23, a detector 8 to detect diffracted X-rays 27 diffracted by the sample 1 and to generate pulses with voltage proportional to the energy of the diffracted X-rays 27 in a number proportional to the intensity thereof, and a linkage means 20 such as a goniometer for linking the drive of the sample support 2 and the detector 8 to accomplish a continuous scan so that the diffracted X-rays 27 are irradiated upon the detector 8 while the sample support 2 is rotated.

More specifically, when the incident X-rays 23 are irradiated upon the sample 1 at a certain incident angle θ, an extension 29 of the incident X-rays 23 and the diffracted X-rays 27 diffracted by the sample 1 forms a diffraction angle 2θ which is twice the incident angle θ. However, the linkage means 20 rotates the sample support 2 to place the sample 1 on the axis O that passes the center of the surface of the sample 1 and is perpendicular to the plane of a sheet of FIG. 3, and, also, rotates the detector 8 along the circular path 12 on the axis O by the angle that is twice the angle of rotation of the sample support 2, so that while the incident angle θ is varied, the diffracted X-rays 27 of the incident angle θ can continue to impinge upon the detector 8. More specifically, the linkage means 20 includes, for example, a worm gear mounted on a drive shaft of a pulse motor, a main rotary shaft fixed concentrically to a worm wheel, meshed with the worm gear, about a common axis O and on which the sample support 2 is mounted, and a mount mechanically coupled with the main rotary shaft and on which the detector 8 is mounted and is adapted to be driven by the pulse motor.

As is the case with the apparatus of the previously described first embodiment, this apparatus also includes a pulse height analyzer 13, a scaler 14, a counting time counter 15, a frequency divider 16 and a correction calculating means 11. It is, however, to be noted that the frequency divider 16 generates a readout signal based on a signal fed from a high resolution (for example, ¹⁄₁₀,₀₀₀ degree) rotary encoder 30 provided on the main rotary shaft of the linkage means 20 in the apparatus of the second embodiment.

Figure 3:
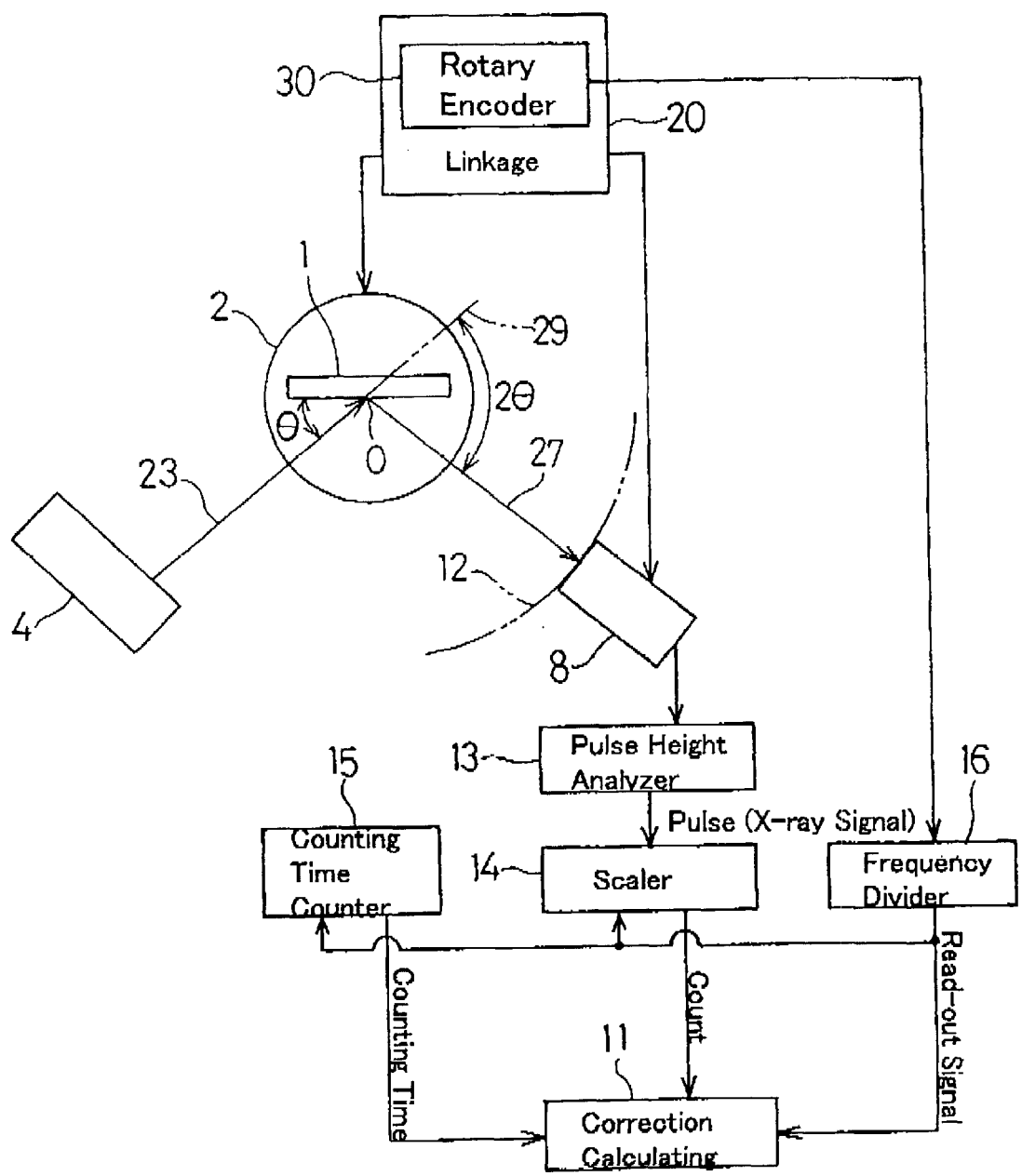
FIG. 3 is a schematic diagram showing an X-ray diffractometer of the second preferred embodiment in the present invention.
Figure 4:
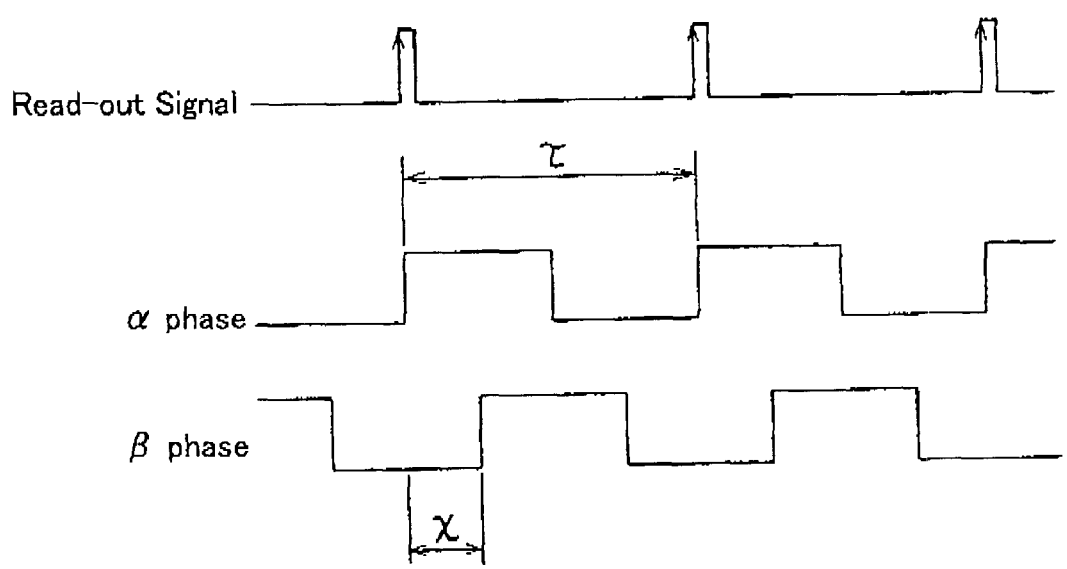
FIG. 4 is a timing chart showing the relationship between two phase signals that are outputs from a rotary encoder employed in the X-ray diffractometer, and a read-out signal that is an output from a frequency divider employed in the X-ray diffractometer.

More specifically, where, for example, the signals from the rotary encoder 30 are, as shown in FIG. 4, two phase square waves α and β which are displaced a ¼ cycle in phase from each other, each of the square waves α and β has a cycle τ corresponding to ⁴⁄₁₀,₀₀₀ degree in terms of θ and also has ON duration of the half cycle, the frequency divider 16 in response to the signals α and β from the rotary encoder 30 outputs the read-out signal to the correction calculating means 11 each time the β phase is OFF and the α phase becomes ON, that is, for a fixed scanning interval in the linkage means 20 shown in FIG. 3 which is ⁴⁄₁₀,₀₀₀ degree in terms of θ, and the correction calculating means 11 reads out the count given by the scaler 14 and the counting time measured by the counting time counter 15 every ⁴⁄₁₀,₀₀₀ degree in terms of θ, so that the count can be corrected by dividing it by the counting time and the corrected count consequently represents the intensity of the diffracted X-ray during that scanning interval. It is to be noted that the fixed scanning interval can be preset to change.

With the apparatus of the second embodiment described above, the counting time counter 15 and the frequency divider 16 are used to determine the counting time for a fixed scanning interval and the correction calculating means 11 is used to correct the count for each scanning interval based on the corresponding counting time. Accordingly, an accurate intensity of the diffracted X-ray for each scanning interval can be obtained and also a rapid and accurate analysis is possible with the continuous scanning technique in the X-ray diffraction analysis. Moreover, since the frequency divider 16 generates the read-out signal based on, not the pulses to be supplied to the pulse motor for driving the linkage means 20, but the signals α and β from the high resolution rotary encoder 30 mounted on the main rotary shaft of the linkage means 20, the count for each scanning interval can also be corrected for an instable condition in which the counting time for each scanning interval flutuates as a result of any possible mechanical processing error and/or a back-lash in the linkage means 20, wherefore a more accurate intensity of the X-ray for each scanning interval can be obtained and a rapid and more accurate analysis can be performed with the continuous scanning in the X-ray diffraction analysis.

Also, in the measurement of the conventional step scan method, it not only requires relatively long time for the measurement, but it gives error caused by the minimum resolution of the rotary encoder in positioning to stop at a specified angle for a fixed time (that is, the position can not be determined within the range χ of ¹⁄₁₀,₀₀₀ deg where the β phase is OFF and the α phase is ON in FIG. 4), the apparatus according to this embodiment is free torn such an error since the read-out signal is generated in response to the detection of the edge (i.e., timing when the pulse changes to ON) in the α phase signal from the rotary encoder 30.

The X-ray fluorescence spectrometer of the third preferred embodiment in the present invention will be described with reference to the drawings. The structure of this apparatus will first be described. As shown in a top view in FIG. 6, this X-ray fluorescence spectrometer includes a measuring unit 18 for irradiating with primary X-rays 3 a band-shaped sample 21 which has a plurality of layers 21a and 21b and is transported in the direction Z lengthwise thereof (in a vertical direction, for example, upwards), to excite the sample 21 so as to emit fluorescent X-rays 5 and generate the pulses in a number proportional to the intensity of the emitted fluorescent X-rays 5 per unitary time.

The sample 21 which is applied to this apparatus is a release coated paper 21 made up of a paper 21b coated with a layer of silicone 21a. The measuring unit 18 consists of a head 19 which includes an X-ray tube for emitting the primary X-rays 3 and a detector for generating the pulses in a number proportional to the intensity of the incident fluorescent X-rays 5 per unitary time, shuttles in the widthwise direction X of the release coated paper 21 along a horizontal rail 42 that is fixed to a floor through legs 41, by means of a pulse motor 43 and a timing belt 44 coupled with a rotary shaft of the pulse motor 43 that are built in the rail 42 as shown in a front view in FIG. 5. In other words, the legs 41, the rail 42, the pulse motor 43 and the timing belt 44 shuttles the measuring unit 18 in the widthwise direction X (the horizontal direction) of the release coated paper 21 that lies perpendicular to the lengthwise direction Z and organize the drive means 40. The measuring unit 18 is electrically connected with a pulse height analyzer 13 and a frequency divider 26 described later by using a flexible flat cable so as to avoid any problem in the movement of the measuring unit 18.

The measuring unit 18 also includes a pair of reflection type photo-sensors 50A and 50B as a sample edge detecting means 50 for detecting the edges A and W of the release coated paper 21. These photo-sensors 50A and 50B are fitted to the measuring unit 18 along the widthwise direction X of the release coated paper 21.

Also, the apparatus in the third embodiment include; as described in the first and second embodiments, a pulse height analyzer 13 for selecting pulses generated by the measuring unit 18 which fall within a fixed range of voltage; a scaler 14 for counting the count of the pulses (i.e., for counting the number of the pulses) selected by the pulse height analyzer 13; and a counting time counter 15 for measuring the time required for the scaler 14 to count the selected pulses; and a correction calculating means 11 for reading out the count given by the scaler 14 and the counting time measured by the counting time counter 15 and correcting the count based on the counting time in response to a read-out signal from a frequency divider 26. It is, however, to be noted that the frequency divider 26 employed in the apparatus in the third embodiment generates the readout signal for each fixed moving range in the drive means 40. The fixed moving range referred to above starts from the position of the measuring unit 18 when the sample edge detecting means 50 detects the edges A and W of the release coated paper 21 in the widthwise direction X thereof.

The apparatus in the third embodiment furthermore includes a coating weight calculating means 60 for calculating the amount of silicone coated of the silicone layer 21a for each of the fixed drive range, based on the count that has been corrected by the correction calculating means 11.

The operation of the apparatus will now be described. With respect to the release coated paper 21 being transported upwardly from a lower position at a fixed speed within the range of for example, 100 to 600 m/min, the measuring unit 18 is first moved from left to right by the drive means 40 at a speed of, for example, 20 mm/sec and when the left edge A of the release coated paper 21 enters in the range between the reflection type photo-sensors 50A and 50B as shown in FIG. 7, that is, when the measuring unit 18 (particularly the center of light receiving part in the head 19) is moved to the position at the left edge A of the release coated paper 21, the frequency divider 26, based on a signal fed from the reflection type photo-sensor assembly 50, resets the count of the scaler 14 and also the counting time of the counting time counter 15 to zero, respectively.

Figure 7:
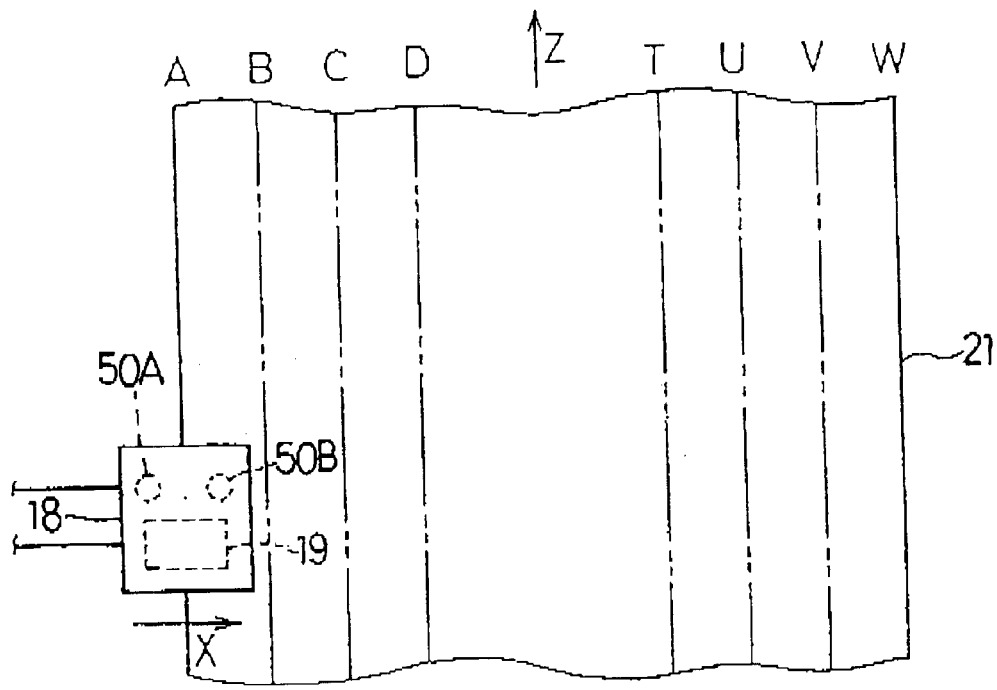
FIG. 7 is a front view of the measurement unit employed in the X-ray fluorescence spectrometer of FIG. 5, which is located leftwards of a sample to be analyzed.

Assuming now that the width of the head 19 is 20 mm in the direction X, the head 19 does not face with the release coated paper in the ranges of 20 mm from the both edges at the left and right sides during the movement as shown in FIG. 7 and accurate intensities can not be obtained. Accordingly, side section A-B and V-W of the release coated paper 21 are dealt with as insensitive sections and are not used for the measurement (even if measured, the date are not used). The remaining portion B to V of the release coated paper 21 excluding the insensitive sections A-B and V-W thereof is divided into a plurality of sections B-C, C-D, . . . T-U and U-V of 20 mm in width each. Starting from the position of the measuring unit 18 where the reflection type photo-sensor assembly 50 detects the edges A or W of the release coated paper 21 in the widthwise direction X thereof, the frequency divider 26 generates the read-out signal for each predetermined moving range in the drive means 40, and the length of this moving range is set to 20 mm which is the same as the length of one section of the release coated paper 21.

Figure 8:
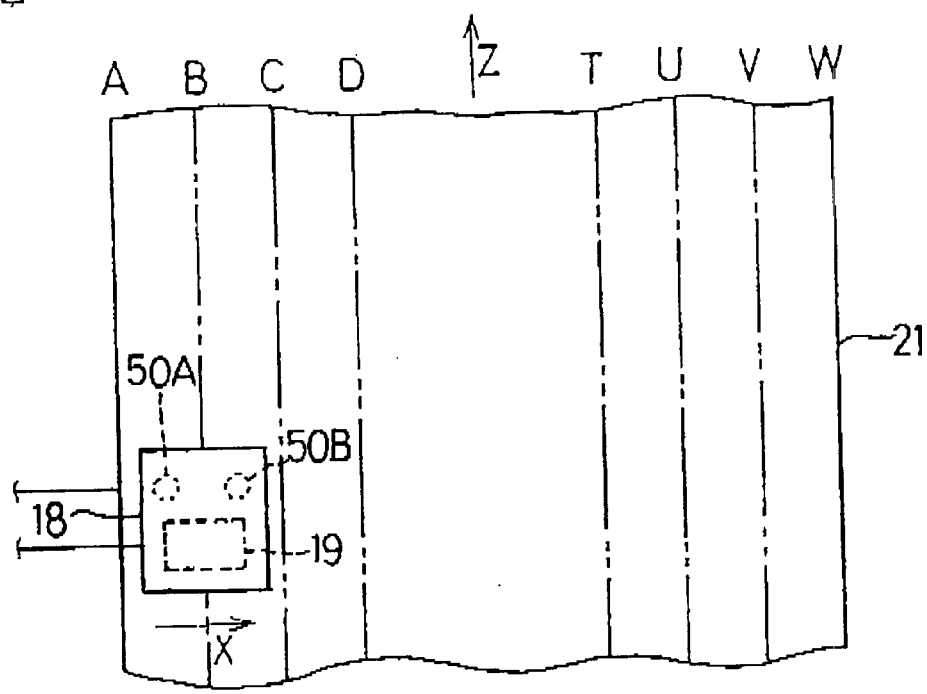
FIG. 8 is a front view of the measurement unit employed in the X-ray fluorescence spectrometer of FIG. 5, which is located leftwards of a section B-C.

Accordingly, when the measuring unit 18 arrives at the position of the left border in the section B-C, that is, a boundary B shown in FIG. 8 after continuous movement of the measuring unit 18, the position is the start of measurement for the section B-C. Thus, when the measuring unit 18 arrives at such position, the frequency divider 26 outputs the read-out signal to the scaler 14 to start counting the number of the pulses and also the counting time counter 15 starts to measure the counting time based on a signal from the rotary encoder 30 indicating that the pulse motor 43 built in the rail 42 shown in FIG. 5 has rotated an accumulated angle corresponding to the distance of 20 mm movement of the measuring unit 18 which is equal to the width of the section A-B from the left edge A of the release coated paper 21.

When the measuring unit 18 arrives at the position of the right border of the section B-C, that is, a boundary C shown in FIG. 9 after further continuous movement of the measuring unit 18, the position is the end of measurement for the section B-C and, the start of measurement of the section C-D at the same time. Thus, when the measuring unit 18 arrives at such position, the frequency divider 26 outputs the read-out signal to the correction calculating means 11 based on a signal from the rotary encoder 30 indicating that the pulse motor 43 built in the rail 42 shown in FIG. 5 has rotated an accumulated angle corresponding to the distance of 40 mm movement of the measuring unit 18 which is equal to the width of the sections A-B and B-C from the left edge A of the release coated paper 21. The scaler 14 resets the count when the count has been read out and starts counting of the number of pulse again, and the counting time counter 15 resets the counting time when the counting time has been read out and starts measurement of the counting time again.

Then, the correction calculating means 11 reads out the count given by the scaler 14, that is, the number of pulses generated by the measuring unit 18 during the movement thereof over the section B-C shown in FIG. 9, and the counting time measured by the counting time counter 15 (FIG. 5), that is, the time required for the measuring unit 18 to move over the section B-C in response to the read-out signal from the frequency divider 26 and the count is divided by the counting time for the correction. Also, the coating weight calculating means 60 shown in FIG. 5, determines the coating weight of the silicone layer 21a in the section B-C of the release coated paper 21 by specifically inserting the corrected count in a predetermined calculating equation based on the count which has thus been corrected by the correction calculating means 11 shown in FIG. 5. It is, however, to be noted that the thickness of the silicone layer 21a can also be determined by changing the predetermined calculating equation.

By repeating the foregoing procedure, the coating weight of the silicone layer in each of the sections C-D, D-E, . . . T-U and U-V is determined. The section V-W is dealt with as an insensitive section and is therefore not used for the measurement as hereinbefore described and, accordingly, when the right edge W of the release coated paper 21 enters in the range between the reflection type photo-sensors 50A and 50B, the direction of movement of the measuring unit 18 by the drive means 40 shown in FIG. 5 is reversed from the rightward direction to the leftward direction in response to a signal from the reflection type photo-sensor assembly 50.

Accordingly, in the coating weight of the silicone layer 21a is determined in the reverse order from the sections U-V, T-U, . . . C-D and B-C in a manner similar to that during the rightward movement of the measuring unit 18 when the measuring unit 18 is moved leftwards. The section A-B is dealt with as an insensitive section and is therefore not used for the measurement as hereinbefore described and, accordingly, when the left edge A of the release coated paper 21 enters in the range between the reflection type photo-sensors 50A and 50B, the direction of movement of the measuring unit 18 by the drive means 40 shown in FIG. 5 is again reversed from the leftward direction to the rightward direction in response to a signal from the reflection type photo-sensor assembly 50.

Figure 5:
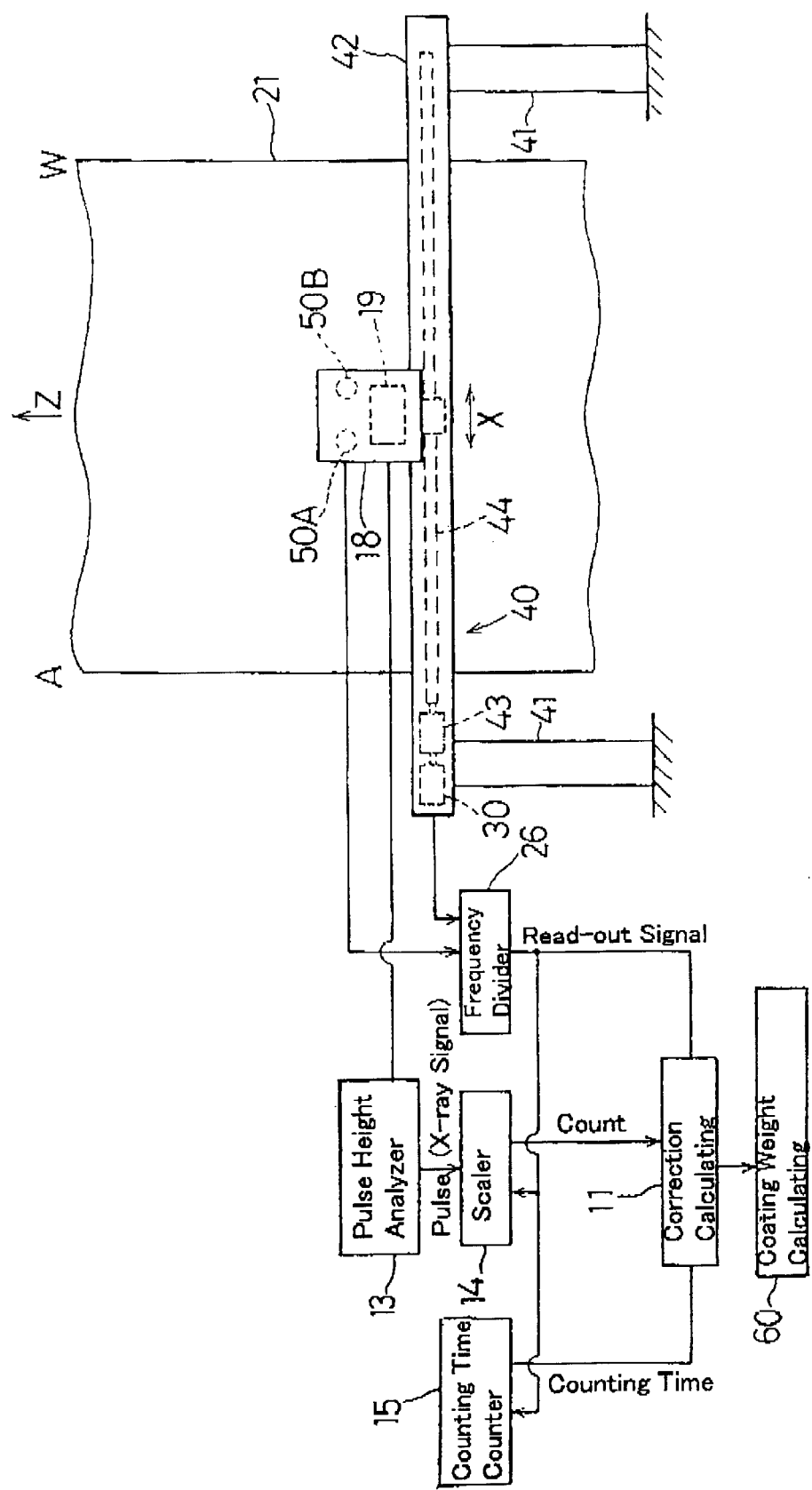
FIG. 5 is a front view of the X-ray fluorescence spectrometer of the third preferred embodiment of the present invention.

Thus, by continuing the shuttle of the measuring unit 18 in the widthwise direction of the release coated paper 21, the coating weight of the silicone layer 21a is determined for each fixed moving range that is, for each section of the release coated paper 21 by the drive means 40 shown in FIG. 5 starting from the left and right edges A and W of the release coated paper 21. It is to be noted that correction of the count and calculation to determine the coating weight of the silicone layer 21a may not be carried out at each time when the measuring unit 18 moves a distance corresponding to each section, but may be collectively done later. It is also to be noted that the sections of the release coated paper 21 may not have an equal width.

As hereinabove described, with the apparatus of this embodiment, the correction calculating means 11 shown in FIG. 5 corrects the count of the pulses generated by the measuring unit 18, based on the counting time which is the time required for the measuring unit 18 to move, for each of the moving ranges from one edge A to the opposite edge W of the release coated paper 21 in the widthwise direction thereof. Accordingly, if the length of the moving interval is set to a value equal to the length of each of the sections that the release coated paper 21 are divided in the widthwise direction X thereof, the coating weight of the silicone layer 21a can be rapidly and accurately determined for each section of the release coated paper 21 without the deviation occurring in correspondence of the coating weight of the silicone layer 21a determined for each moving range with the section of the release coated paper 21 even if the speed varies in high moving speed of the measuring unit 18. Thus, the rapid and accurate analysis is possible with the continuous scanning in the fluorescent X-ray analysis.

If the position of the moving part is estimated based on the moving of time from one edge of the sample as used in the conventional technique described above, the position estimated will deviate from the actual position since the speed of movement is not constant. Accordingly, it may occur that in a section neighboring the insensitive region and odd measured data which are different from the fixed moving time can be obtained and such odd measured data are inaccurate and cannot be adopted together with the measurement data in the insensitive region, resulting in the increase of useless measurement. In contrast thereto, with the apparatus of this embodiment, the count of the pulses generated by the measuring unit 18 is corrected based on the counting time which is the time required for the measuring unit 18 to move for each moving interval from each of the edges A and W of the release coated paper 21 in the widthwise direction X thereof. Therefore, no odd measurement data as described above will not be produced without useless measurement if the length of the moving interval is set to a value equal to the length of each section of the release coated paper 21.

Figure 6:
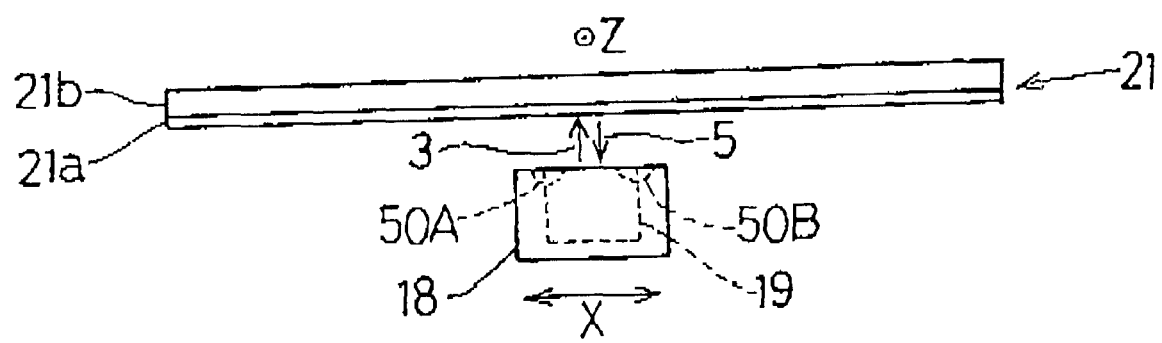
FIG. 6 is a top view of a measurement unit employed in the X-ray fluorescence spectrometer shown in FIG. 5.

Furthermore, the apparatus of this embodiment can be satisfactonrily applied to the sample 21 of, for example, a magnetic tape 21 shown in FIG. 6. The magnetic tape 21 is a plastic film made of PET (polyethylene telephtalate), and a magnetic material 21a of Fe and a magnetic material 21c (not shown, coated on the same side as 21a of the plastic film 21b) of FeCo are coated (painted or vacuum evaporated), and it can also be applied to a plurality of layers of which coating weight or thickness for each layer to be determined and they are Fe coated layer 21 and FeCo layer 21c. In such case, the intensities of the fluorescent X-rays 5 emitted from each of Fe and Co are measured in a manner similar to that described hereinabove, and the coating weight or thickness of each of the layers 21a and 21c is determined. Also, the magnetic tape being transported may have the both edge portions in the widthwise direction thereof on which neither the magnetic layer 21a nor the magnetic layer 21c is coated and on which the PET film is exposed and, accordingly, those both edge portions of the magnetic tape are not included in the sample to be analyzed by the apparatus in the present invention. In other words, the edge of the magnetic tape 21 in the widthwise direction thereof where the magnetic tape 21 is detected by the reflection type photo-sensors 50A and 50B is the edge of the magnetic tape 21 where the first and second magnetic layers 21a and 21c are coated.

Also, the apparatus of the present invention can be applied to the sample which the entire sample is transparent such as a sealing film made up of a plastic film of, for example, PET on which $SiO_2$ and $Al_2O_3$ are coated (vacuum evaporated). In such case, the edges of the sample in the widthwise direction thereof can be detected by using, an ultrasonic sensor in place of the previously discribed reflection type photo-sensors.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

What is claimed is:

1. An X-ray fluorescence spectrometer which comprises:
   a sample support for supporting thereon a sample to be analyzed;
   an X-ray source for irradiating the sample with primary X-rays to excite the sample to emit fluorescent X-rays therefrom;
   a spectroscopic device for monochromating the fluorescent X-rays emitted from the sample;
   a detector adapted to detect the fluorescent X-rays, which have been monochromated by the spectroscopic device, and to generate pulses of a voltage proportional to an energy of the fluorescent X-rays in a number proportional to an intensity of the fluorescent X-rays;
   a linkage means for linking the drive of the spectroscopic device and the detector to scan the sample and the detector continuously, by causing the monochromated fluorescent X-rays to be irradiated upon the detector while a wavelength of the fluorescent X-rays monochromated by the spectroscopic device varies;
   a pulse height analyzer for selecting the pulses, generated by the detector, which fall within a fixed voltage range;
   a scaler for determining a count of the pulses selected by the pulse height analyzer;
   a counting time counter for measuring a counting time required for the scaler to determine the count of the pulses;
   a frequency divider for generating a read-out signal for each of fixed scanning intervals in the linkage means; and
   a correction calculating means operable in response to the read-out signal from the frequency divider to read out the count of the pulses, determined by the scaler, and the counting time measured by the counting time counter, to correct the count of the pulses based on the counting time.

2. The X-ray fluorescence spectrometer as claimed in claim 1, wherein the linkage means includes a rotary encoder and wherein the frequency divider generates the read-out signal based on a signal fed from the rotary encoder in the linkage means.

3. An X-ray diffractometer which comprises:
   sample support for supporting thereon a sample to be analyzed;
   an X-ray source for irradiating the sample with incident X-rays;
   a detector adapted to detect X-rays, which have been diffracted by the sample, and to generate pulses of a voltage proportional to an energy of the diffracted X-rays in a number proportional to an intensity of the diffracted X-rays;
   a linkage means for linking the drive of the sample support and the detector to scan the sample and the detector continuously, by rotating the sample support to cause the diffracted X-rays to be irradiated upon the detector;
   a pulse height analyzer for selecting the pulses, generated by the detector, which fall within a fixed voltage range;
   a scaler for determining a count of the pulses selected by the pulse height analyzer;
   a counting time counter for measuring a counting time required for the scaler to determine the count of the pulses;
   a frequency divider for generating a read-out signal for each of fixed scanning intervals in the linkage means; and
   a correction calculating means operable in response to the read-out signal from the frequency divider to read out the count of the pulses, determined by the scaler, and the counting time measured by the counting time counter, to correct the count of the pulses based on the counting time.

4. The X-ray diffractometer as claimed in claim 3, wherein the linkage means includes a rotary encoder and wherein the frequency divider generates the read-out signal based on a signal fed from the rotary encoder in the linkage means.

5. An X-ray fluorescence spectrometer which comprises:

a measuring unit for irradiating with primary X-rays a band-shaped sample made up of plural layers and being transported in a direction lengthwise thereof, to excite the sample to emit fluorescent X-rays and for generating pulses in a number proportional to an intensity of the fluorescent X-rays emitted from the sample;

a drive means for shuttling the measuring unit in a direction widthwise of the sample that lies perpendicular to the lengthwise direction of the sample;

a sample edge detecting means mounted on the measuring unit for detecting each of both edges of the sample in the widthwise direction thereof;

a pulse height analyzer for selecting the pulses, generated by the measuring unit, which fall within a fixed voltage range;

a scaler for determining a count of the pulses selected by the pulse height analyzer;

a counting time counter for measuring a counting time required for the scaler to determine the count of the pulse;

a frequency divider for generating a read-out signal for each of fixed moving ranges in the drive means, starting from a position where the sample edge detecting means detects one of the both edges of the sample in the widthwise direction thereof;

a correction calculating means operable in response to the read-out signal from the frequency divider to read out the count of the pulses, determined by the scaler, and the counting time measured by the counting time counter, to correct the count of the pulses based on the counting time; and a coating weight calculating means for determining a coating weight or thickness of at least one of the plural layers, for each of the fixed moving ranges, based on the count corrected by the correction calculating means.

6. The X-ray fluorescence spectrometer as claimed in claim 5, wherein the drive means includes a rotary encoder and wherein the frequency divider generates the read-out signal based on a signal fed from the rotary encoder in the drive means.

7. The X-ray fluorescence spectrometer as claimed in claim 5, wherein the sample is a release coated paper including a paper on which silicone is coated and wherein said one of the plural layers of which coating weight or thickness is determined is a layer of silicone coated.

8. The X-ray fluorescence spectrometer as claimed in claim 5, wherein the sample is a magnetic tape including a plastic film coated with a magnetic material and wherein said one of the plural layers of which coating weight or thickness is determined is a layer of the magnetic material coated.

* * * * *